(12) United States Patent
Krumrey et al.

(10) Patent No.: US 7,087,795 B2
(45) Date of Patent: Aug. 8, 2006

(54) METHOD FOR THE PRODUCTION OF ALDEHYDES

(75) Inventors: Thomas Krumrey, Ratingen (DE); Kurt Schalapski, Oberhausen (DE); Robert Rapier, Ponca City, OK (US); John Steinbach, Bay City, TX (US); Bak Shah, Bay City, TX (US); Mark Hewlett, Bay City, TX (US)

(73) Assignee: Celanese Chemicals Europe GmbH (DE)

( * ) Notice: Subject to any disclaimer, the term of this patent is extended or adjusted under 35 U.S.C. 154(b) by 44 days.

(21) Appl. No.: 10/497,356

(22) PCT Filed: Nov. 27, 2002

(86) PCT No.: PCT/EP02/13340

§ 371 (c)(1),
(2), (4) Date: Sep. 16, 2004

(87) PCT Pub. No.: WO03/050068

PCT Pub. Date: Jun. 19, 2003

(65) Prior Publication Data

US 2005/0065379 A1     Mar. 24, 2005

(30) Foreign Application Priority Data

Dec. 8, 2001   (DE) ................................ 101 60 368

(51) Int. Cl.
*C07C 45/50* (2006.01)
(52) U.S. Cl. ...................................... 568/429; 568/454
(58) Field of Classification Search ................ 568/429, 568/454
See application file for complete search history.

(56) References Cited

U.S. PATENT DOCUMENTS

| 3,357,809 | A | * | 12/1967 | Colchagoff | .................. | 65/229 |
| 4,148,830 | A | * | 4/1979 | Pruett et al. | ................. | 568/454 |
| 4,247,486 | A | * | 1/1981 | Brewester et al. | .......... | 568/454 |
| 5,105,018 | A | | 4/1992 | Miyazawa et al. | | |
| 5,426,238 | A | * | 6/1995 | Mori et al. | ................. | 568/454 |

FOREIGN PATENT DOCUMENTS

| DE | 690 05 715 T2 | 12/1990 |
| DE | 44 19 898 A1 | 12/1994 |
| DE | 199 54 665 A1 | 6/2001 |

* cited by examiner

*Primary Examiner*—Johann R. Richter
*Assistant Examiner*—Sikarl A. Witherspoon
(74) *Attorney, Agent, or Firm*—Charles A. Muserlian

(57) ABSTRACT

The invention relates to a hydroformylation method, whereby the homogeneous liquid reactor discharge is first supplied to a gas/liquid separator and then run through an extraction column with a counter-current of synthesis gas and finally fed to an evaporator. The invention is characterised in that the homogeneous liquid mass flow is supplied to the upper section of the extraction column at a temperature above 90° C.

12 Claims, 2 Drawing Sheets

METHOD FOR THE PRODUCTION OF ALDEHYDES

This application is a 371 of PCT/EP02/13340 filed Nov. 27, 2002.

The invention relates to a process for the hydroformylation of olefinically unsaturated compounds, in which the homogeneous, liquid mixture comprising catalyst and aldehyde which leaves the hydroformylation reactor is treated in countercurrent with synthesis gas at elevated temperature in a downstream extraction column.

It is known that compounds containing olefinic double bonds can be reacted with carbon monoxide and hydrogen to form aldehydes (oxo process). The process is not restricted to the use of olefinic hydrocarbons, but can also be applied to starting materials which contain not only a double bond but further functional groups, preferably ones which remain unchanged under the reaction conditions.

The classical oxo process employs cobalt as catalyst. Its effectiveness is based on the formation of cobalt carbonyl compounds by action of hydrogen and carbon monoxide on metallic cobalt or cobalt compounds at pressures above 20 MPa and temperatures of about 120° C. and above.

In the course of the further development of the oxo process, cobalt has increasingly been replaced by rhodium as catalyst metal. Rhodium is used as a complex comprising not only carbon monoxide but also, preferably, organic phosphines as ligands. Rhodium as metal allows the reaction to be carried out at low pressures. In addition, higher yields are achieved and the unbranched products which are more valuable for further processing are preferentially formed if straight-chain terminal olefins are used as starting materials.

Such a process is known from U.S. Pat. No. 3,527,809 under the name "low-pressure rhodium process". An improved version of this process is disclosed in U.S. Pat. No. 4,148,830. According to this disclosure, the catalyst life and the yield of linear aldehydes can be increased if the high-boiling condensation products of the aldehydes formed are used as solvent for the catalyst and the organic phosphine present in excess. In this process, the precipitation of insoluble rhodium compounds is avoided and the dissolved catalyst can be reused over many catalysis cycles without a decrease in the activity being observed. In the process known from U.S. Pat. No. 4,148,830, the liquid output from the hydroformylation reactor is firstly cooled and, after depressurization, passed through a gas/liquid separator, resulting in hydrogen dissolved in the crude aldehyde, dissolved carbon monoxide and unreacted olefinic compounds vaporizing. The catalyst-containing crude aldehyde is subsequently passed through a vaporizer where the crude aldehyde is obtained as top fraction and a rhodium-containing residue comprising free phosphine ligands, residual aldehyde and relatively high-boiling aldehyde condensation products is obtained. The latter can be recirculated to the hydroformylation process. The aldehyde-containing top product obtained in the catalyst separation is purified further in a downstream distillation and separated into the n and iso compounds. The process known from U.S. Pat. No. 4,148,830 is also referred to as "hydroformylation process with liquid recycle".

A further hydroformylation process carried out in the presence of rhodium and organic phosphines is known from U.S. Pat. No. 4,247,486. In this process variant, a gaseous product stream comprising olefinically unsaturated compound, hydrogen, vaporized crude aldehyde and its condensation products is taken from the reactor. This gaseous product stream is condensed and passed to a separation vessel in which the crude aldehyde separates out from the volatile constituents. The volatile constituents, essentially hydrogen, carbon monoxide, the olefinically unsaturated compound and its hydrogenation products, are, after separating off the hydrogenation products, for example the alkanes, recirculated to the hydroformylation reactor. The amount of gas recirculated per unit time is such that the liquid volume in the hydroformylation reactor remains constant. Furthermore, the amount of aldehyde condensation products removed with the gaseous output from the reactor corresponds to the amount formed in the hydroformylation reaction. The process known from U.S. Pat. No. 4,247,486 is also referred to as "hydroformylation process with gas recycle".

Hydroformylation processes in which the offgas from a first hydroformylation stage is reacted further in a second hydroformylation stage are likewise known. Such a process is described in EP-A1-0 188 246. The first stage is carried out with recirculation of liquid, as known from U.S. Pat. No. 4,148,830, and the offgas obtained is fed to a second, decoupled stage, i.e. a secondary stage operated-separately from the first stage, in which the offgas from the first hydroformylation stage together with added carbon monoxide and hydrogen is reacted and liquid or gas is recirculated.

EP 0188 246 points out that in the first hydroformylation stage carried out with recirculation of liquid, olefinically unsaturated compounds and synthesis gas are present in dissolved form in the solution obtained in the downstream gas/liquid separator. These and further volatile constituents can be distilled off together with crude aldehyde from the catalyst solution in the vaporizer and partly condense in the crude aldehyde. In the subsequent purification of the crude aldehyde to separate it into n and iso isomers, these volatile compounds are recovered and returned to the hydroformylation process.

The volatile constituents which have not been condensed in the crude aldehyde during the separation of the crude aldehyde from the catalyst solution are separated off, compressed and returned directly to the hydroformylation process.

U.S. Pat. No. 5,105,018 likewise relates to a two-stage hydroformylation process in which the gaseous or liquid/gaseous output from the reactor of the first reaction stage is firstly cooled and subsequently fed into a gas/liquid separator from which the offgas is recirculated to the first hydroformylation stage while the cooled solution, which contains dissolved starting olefin, is treated in countercurrent with synthesis gas in an extraction column, resulting in dissolved olefin being stripped out. This olefin is recirculated together with synthesis gas to the first hydroformylation stage. The offgas from the first hydroformylation stage is passed to a second hydroformylation stage in which the gas/liquid reactor output is likewise firstly cooled and passed to a gas/liquid separator. The liquid comprising crude aldehyde and catalyst solution which is obtained in the gas/liquid separator of the second hydroformylation stage is combined with the solution obtained after the synthesis gas extraction in the first stage and passed to a vaporizer in which crude aldehyde and catalyst solution are separated. The catalyst solution is returned to the first and second hydroformylation stages.

Cooling the liquid reactor output, which has been heated to the reaction temperature, to 60 or 80° C. and passing it to a gas/liquid separator is known from the prior art. The liquid stream obtained in this way contains a considerable amount of unreacted olefinic starting compound which is, according to the prior art, removed from the liquid by means of an extraction column operated using synthesis gas and is recirculated to the hydroformylation reactor.

However, a large residual amount of olefinically unsaturated compound in the reaction product obtained after the gas/liquid separator has an adverse effect on the subsequent work-up and separation steps. A high residual content of olefinically unsaturated compound makes it necessary for a large amount of synthesis gas to be fed at high pressure into the extraction column in order to achieve essentially complete stripping of the dissolved olefinically unsaturated compound. Such essentially complete removal of the volatile olefinic compounds is advantageous for the operation of the downstream separation of the crude aldehyde from the catalyst solution by distillation and for the purification of the n- and iso-aldehydes by distillation, since high residual contents of volatile olefinic compounds have an adverse effect on the temperature and pressure conditions in these downstream distillations. The olefinic compound recovered at these points of the process firstly has to be compressed with a high consumption of energy in order to be able to be returned to the hydroformylation reactor. In general, the liquid, homogeneous solution obtained in the gas/liquid separator contains up to 10% by weight, frequently up to 8% by weight, of olefinically unsaturated compound, based on the total solution. It is desirable to convert this residual amount of olefinically unsaturated compound as simply as possible into valuable aldehyde product so as to keep the residual content of volatile olefinic compounds in the liquid streams which are fed to work-up by distillation as small as possible and thus avoid the abovementioned disadvantages.

It is therefore an object of the invention to provide a hydroformylation process for olefinically unsaturated compounds, in which the residual amount of olefinically unsaturated compound present in the liquid, homogeneous reactor output is converted as simply as possible into aldehydes and the residual content of olefinically unsaturated compound in the liquid streams passed to work-up by distillation is thereby reduced.

This object is achieved by a process for reacting olefinically unsaturated compounds with synthesis gas in the presence of a catalyst solution comprising rhodium and organic phosphorus(III) compounds in a hydroformylation reactor, in which the homogeneous, liquid reactor output comprising crude aldehyde and catalyst is passed to a gas/liquid separator and the homogeneous, liquid stream obtained is treated in an extraction column operated in countercurrent with synthesis gas and the liquid output from the extraction column is fed into a vaporizer in which crude aldehyde and catalyst solution are separated from one another. In the process of the present invention the homogeneous, liquid stream obtained after the gas/liquid separator is, if desired after addition of synthesis gas, introduced at a temperature above 90° C., preferably from 110 to 150° C., into the upper part of the extraction column.

The hydroformylation process of the invention is carried out with recirculation of liquid. The liquid reactor output is firstly passed without cooling through a gas/liquid separator in which the gaseous components evaporate from the liquid stream and are removed as offgas from the reaction system. In the gas/liquid separator, the temperature of the homogeneous, liquid reactor output is established; it is generally above 90° C., usually in the range from 110 to 150° C. The pressure conditions correspond to those in the hydroformylation reactor.

The liquid stream comprising crude aldehyde and catalyst solution which leaves the gas/liquid separator further comprises dissolved synthesis gas and olefinically unsaturated compound. In general, the content of olefinically unsaturated compound is up to 10% by weight, in most cases 4–8% by weight, based on the homogeneous reaction mixture.

In contrast to the teachings of the prior art, the liquid reactor output is passed without cooling to the gas/liquid separator. It is important that the homogeneous solution obtained after the liquid separator is introduced at a temperature of above 90° C., preferably from 110 to 150° C. and in particular from 115 to 145° C., into the upper part of the extraction column.

The introduction into the upper part of the extraction column is preferably carried out on the 1st tray, counted from the top of the column. Synthesis gas flows from the bottom toward the liquid mixture of crude aldehyde and catalyst solution and is taken off at the top of the extraction column and recirculated to the hydroformylation reactor. The extraction column is generally operated at a temperature which is somewhat below the reactor temperature. It is generally from 80 to 120° C., preferably from 90 to 110° C.

Since synthesis gas has to be passed under pressure through the extraction column and into the hydroformylation reactor, a synthesis gas pressure higher than that in the hydroformylation reactor has to be set in the extraction column. This pressure generally exceeds the pressure in the hydroformylation reactor by from 0.1 to 1.0 MPa.

As a result of the introduction according to the invention of the homogeneous solution obtained after the gas/liquid separator into the extraction column at elevated temperature, further reaction of the dissolved olefinically unsaturated compound with the synthesis gas passed through in countercurrent occurs in the presence of the catalyst solution to form aldehydes. In the process of the invention, the extraction column thus acts both as distillation column for separating off olefinically unsaturated compounds via the top of the extraction column and as reaction column in which the olefinically unsaturated compounds react to form less volatile aldehydes which are taken off with the liquid discharged at the bottom of the extraction column and passed to the crude aldehyde vaporizer.

Since it is necessary not only for the olefinically unsaturated compound to be distilled off in the extraction column but also for the conversion into aldehydes to occur, it has to be ensured that the temperature in the extraction column is maintained at a sufficiently high level for the hydroformylation reaction to be maintained. This is generally achieved sufficiently well by the heat of reaction liberated by the reaction in the extraction column. As a result of the introduction of the homogeneous solution into the upper part of the extraction column at a temperature of above 90° C., preferably in the range from 110 to 150° C., the reaction temperature necessary for the hydroformylation reaction can be maintained in the extraction column over a zone of about 20%, based on the length of the extraction column and measured from the top of the column.

Since the vaporization of the olefinically unsaturated compound in the extraction column has a cooling action, it can prove to be advantageous to admix the liquid homogeneous solution to be introduced into the extraction column with synthesis gas upstream in the feed line and then to introduce it into the extraction column. Since the liquid, homogeneous reactor output is not cooled and is at a temperature which is only a little below the actual hydroformylation temperature, further reaction between the dissolved olefinically unsaturated compound and the added synthesis gas occurs with liberation of heat of reaction in the feed line to the extraction column due to the presence of dissolved catalyst. Since the residence time in the feed line to the extraction column is only short and the solution which has been additionally heated by the heat of reaction liberated is introduced virtually immediately into the extraction column, damage to the catalyst at this point of the process does not have to be feared. Introduction of the homogeneous, liquid solution which has been additionally heated by the heat of reaction into the extraction column allows the temperature profile in the extraction column to be increased further in a simple manner. As a result, the homogeneous liquid stream also leaves the extraction column at a higher temperature, so that a small energy input is required in the downstream vaporizer for separation of crude aldehyde and catalyst.

By employing the extraction column to remove the olefinically unsaturated compound not just through a physical distillation process but through further conversion of olefinically unsaturated compound into aldehyde by reaction with synthesis gas, the invention provides manifold advantages. Since the liquid stream introduced into the extraction column is not cooled but is instead introduced at elevated temperature and the heat of reaction liberated provides additional heat energy, the extraction column can be operated at elevated temperature without an additional external energy source being required. The olefinically unsaturated compound can therefore be removed to a substantial extent in the extraction column operated at elevated temperature, so that the residual content of olefinically unsaturated compound in the liquid stream leaving the extraction column is reduced, resulting in the advantage that less olefinically unsaturated compound goes to the subsequent crude aldehyde vaporizer and from there to the downstream process steps. In general, the residual content of olefinically unsaturated compound in the homogeneous solution introduced into the crude aldehyde vaporizer is less than 0.7% by weight, preferably less than 0.5% by weight, in each case based on the homogeneous solution. Since further reaction of the olefinically unsaturated compound to form aldehyde occurs in the extraction column, the measure according to the invention leads to an increase in the effective reactor volume and thus in a very simple manner to an increase in capacity. Finally, heat of reaction is introduced into the homogeneous liquid output from the extraction column which can then be passed at elevated temperature to the crude aldehyde vaporizer. In this way, the external energy requirement in-the crude aldehyde vaporizer can be reduced.

Extraction columns which are packed with packing elements such as rings or saddles or steel helices are particularly suitable for carrying out the process of the invention. In general, the extraction column has from 10 to 40, preferably from 15 to 25, theoretical plates.

The liquid stream comprising catalyst and crude aldehyde which leaves the extraction column at the bottom is passed to a vaporizer in which crude aldehyde is taken off at the top while the catalyst solution is obtained as bottoms and is returned to the hydroformylation reactor. Since the homogeneous, liquid stream introduced into the vaporizer contains only small residual amounts of olefinically unsaturated compound due to the above-described measures according to the invention, the pressure and temperature conditions in the vaporizer can advantageously be set to generally from 115 to 160° C. and from subatmospheric pressure to atmospheric pressure. The conditions are advantageously chosen so that very small amounts of organic phosphorus(III) compounds and rhodium are carried out at the top and thermal decomposition of rhodium complexes in the vaporizer is largely avoided.

The crude aldehyde which has been separated off is worked up by distillation in a manner known per se and separated into n- and iso-aldehyde.

The hydroformylation is carried out in a homogeneous reaction system. The term homogeneous reaction system refers to a homogeneous solution composed essentially of solvent, catalyst, olefinically unsaturated compound and reaction product. Particularly effective solvents have been found to be the relatively high-boiling condensation products of the aldehydes to be prepared, in particular the trimers and tetramers of the aldehydes to be prepared, which are obtained as by-products in the hydroformylation, and also their mixtures with the aldehydes to be prepared, so that further addition of solvent is not absolutely necessary. In some cases, however, addition of a solvent can prove to be advantageous. As solvents, use is made of organic compounds in which starting material, reaction product and catalyst system are soluble. Examples of such compounds are aromatic hydrocarbons such as benzene and toluene or the xylenes. Other solvents which can be used are paraffin oil, cyclohexane, n-hexane, n-heptane or n-octane, ethers such as tetrahydrofuran, ketones, Texanol® from Eastman or alkylenediols such as ethylene glycol, diethylene glycol, triethylene glycol, 1,2-propanediol, 1,4-butanediol or alkylene glycols having a mean molar mass in the range from 200 to 1000 g/mol. The proportion of the solvent in the reaction medium can be varied over a wide range and is usually from 20 to 90% by weight, preferably from 50 to 80% by weight, based on the reaction mixture.

Catalysts used are rhodium complexes which contain organic phosphorus(III) compounds as ligands. Such complexes and their preparation are known (e.g. from U.S. Pat. Nos. 3,527,809, 4,148,830, 4,247,486, 4,283,562). They can be used as chemically uniform complexes or as a mixture of different complexes. The rhodium concentration in the reaction medium extends over a range from about 1 to about 1000 ppm by weight and is preferably from 10 to 800 ppm by weight. In particular rhodium is used in concentrations of from 100 to 700 ppm by weight, in each case based on the homogeneous reaction solution. The stoichiometric rhodium complex can be employed as catalyst. However, it has been found to be advantageous to carry out the hydroformylation in the presence of a catalyst system comprising rhodium-phosphorus complex and free, i.e. excess, phosphorus ligand which no longer forms a complex with rhodium. The free phosphorus ligand can be the same one as in the rhodium complex, but it is also possible to use ligands different from this. The free ligand can be a chemically uniform compound or consist of a mixture of various organic phosphorus(III) compounds. Examples of rhodium-phosphorus complexes which can be employed as catalysts are described in U.S. Pat. No. 3,527,809. Preferred ligands in the catalytic rhodium complexes include, for example, triarylphosphines such as triphenylphosphine, trialkylphosphines such as tri (n-octyl)phosphine, trilaurylphosphine, tri(cyclohexyl)phosphine, alkylphenylphosphines, cyclo-alkylphenylphosphines and diphosphines, in particular diphosphines containing an aromatic radical, for example 2,2'-bis(diphenylphosphino)biphenyl, 2,2'-bis(diphenylphosphino)binaphthyl, 2,2'-bis(diphenylphosphinomethyl)biphenyl or 2,2'-bis(diphenylphosphinomethyl)binaphthyl.

Owing to its ready availability, triphenylphosphine is employed particularly frequently. Apart from the organic phosphines, it is also possible to use organic phosphites and diphosphites as organic phosphorus(III) compounds.

The concentration of organic phosphorus(III) compounds is generally from 15 to 60% by weight, based on the homogeneous reaction solution. Preference is given to using a concentration of organic phosphorus(III) compounds in the range from 25 to 50% by weight, in particular from 30 to 40% by weight, in each case based on the homogeneous reaction solution. Surprisingly, a shift in the n-/i-aldehyde ratio in the direction of the n-aldehyde is observed as the concentration of organic phosphorus(III) compounds increases.

The hydroformylation conditions can vary within wide limits and can be matched to individual circumstances. They depend, inter alia, on the starting material or on the catalyst system chosen. The hydroformylation of the starting materials is usually carried out at temperatures of from 90 to 150° C. Temperatures of from 110 to 150° C., in particular from 120 to 140° C., are preferably employed. The total pressure extends over a range from 0.1 to 10 MPa, preferably from 1 to 5 MPa and in particular from 2 to 2.5 MPa.

In general, the catalyst is formed from the components rhodium or rhodium compound and organic phosphorus(III) compound in the presence of synthesis gas in a preformation step. Particularly useful solvents for carrying out the preformation have been found to be the high-boiling condensation products of the aldehydes. Further suitable solvents are alkylene glycols such as ethylene glycol or 1,2-propanediol. The conditions of the preformation step generally correspond to the conditions in the hydroformylation step. The preformation conditions can be set when starting up the hydroformylation process so that the olefinically unsaturated compound is only added when the active rhodium catalyst has been formed. If rhodium is added while the process is running, a solution of the active rhodium-phosphorus(III) complex firstly has to be prepared in a separate preformation step and is subsequently introduced into the process. In this case, the preformation step is preferably carried out using the solvent which has already been used in the hydroformylation step.

The hydroformylation reaction can be carried out in the known reactor embodiments, e.g. in a stirred reactor, tube reactor, multichamber reactor or loop reactor.

The composition of the synthesis gas fed in can be varied over a wide range. The molar ratio of hydrogen to carbon monoxide is usually from 1:10 to 10:1; mixtures comprising hydrogen and carbon monoxide in a molar ratio of from 3:1 to 1:3, in particular about 1:1, are particularly suitable. However, it can also prove to be advantageous to use a hydrogen-rich synthesis gas. A high proportion of hydrogen has a stabilizing effect on the catalyst system.

The point at which the synthesis gas is introduced into the hydroformylation reactor can also be varied, with synthesis gas being fed into the hydroformylation reactor at one or more feed points. Apart from the customary introduction of synthesis gas via the lower part of the reactor, preferably via the bottom of the reactor, synthesis gas can, in a further process variant, be introduced into the middle part of the hydroformylation reactor. It is possible to introduce all of the synthesis gas via the bottom part or via the middle part of the hydroformylation reactor or part of the synthesis gas is fed in via the lower part and the other synthesis gas substream is fed in via the middle part of the hydroformylation reactor. For feeding in the synthesis gas, all of the fresh synthesis gas introduced into the process can firstly be fed into the extraction column and the synthesis gas which is taken off from the upper part of the extraction column and is laden with olefinically unsaturated compound can be fed into the hydroformylation reactor. However, it is also possible for the stream of fresh synthesis gas firstly to be divided and a substream which is firstly conveyed via the extraction column to be fed into the reactor while the other substream of fresh synthesis gas is introduced directly into the hydroformylation reactor. The ratio of the substreams can be varied over a wide range. In general, the freshly introduced synthesis gas is divided so that equal amounts of synthesis gas are fed in via the two substreams.

The total amount of synthesis gas fed in per unit time and the amount of synthesis gas fed in via the abovementioned substreams depends on the respective reactor dimensions and can be determined by means of simple experiments.

In a particular embodiment of the process of the invention, the synthesis gas which is recirculated from the extraction column is fed in via the bottom of the reactor while fresh synthesis gas is introduced into the middle part of the hydroformylation reactor. The middle region of the hydroformylation reactor into which the synthesis gas is introduced extends in a zone above and below the center point of the hydroformylation reactor and occupies up to 30%, preferably up to 20%, of the total length of the reactor.

The introduction of synthesis gas into the middle part of the hydroformylation reactor surprisingly leads to a significant increase in the conversion of olefinically unsaturated compound into aldehydes and also to an increase in the selectivity to the straight-chain aldehydes.

In a further embodiment of the process of the invention, synthesis gas is added to the liquid, homogeneous stream obtained from the gas/liquid separator before this stream enters the extraction column. The addition of synthesis gas leads to further reaction of the olefinically unsaturated compound to form aldehydes with liberation of heat of reaction in the feed line to the extraction column, so that the temperature of the liquid stream can be increased again before it enters the extraction column without an external energy supply. The synthesis gas quantity fed into the extraction column is generally 5–40% and preferably 10–20% of the synthesis gas quantity fed into the hydroformylation reactor.

The process of the invention can be applied to olefinically unsaturated compounds having any structure. Accordingly, it is possible to use olefins having an internal or terminal double bond and likewise straight-chain or branched olefins as starting material. Furthermore, the olefins can also contain functional groups, in particular groups which are not changed during the course of the reaction. Multiply olefinically unsaturated compounds, e.g., 1,3-butadiene or 1,3-pentadiene are also possible as starting materials. The process of the invention has been found to be particularly useful for the hydroformylation of olefinically unsaturated hydrocarbons having from 3 to 12 carbon atoms in the molecule, preferably propylene and the isomeric butenes which are available industrially as raffinate II, viz. a mixture of 1-butene and 2-butene, or as raffinate III, viz. raffinate II which has been depleted in 1-butene. However, a $C_8$-olefin mixture comprising 2-octene and/or 3-octene can also be used as starting compound in the process of the invention. Industrially available olefin mixtures such as Dimersol® or Octol® or propylene trimer can also be reacted in the process of the invention.

Rhodium is used either as metal or as compound. In metallic form, it is used either as finely divided particles or as a thin layer deposited on a support such as activated carbon, calcium carbonate, aluminum silicate, alumina. Suitable rhodium compounds are salts of aliphatic monocarboxylic and polycarboxylic acids, e.g. rhodium 2-ethylhexanoate, rhodium acetate, rhodium oxalate, rhodium propionate or rhodium malonate. It is also possible to use rhodium salts of inorganic hydrogen or oxygen acids, e.g.

rhodium nitrate or rhodium sulfate, the various rhodium oxides or else rhodium carbonyl compounds such as $Rh_3(CO)_{12}$ or $Rh_6(CO)_{16}$ or complexes of rhodium, e.g. cyclooctadienylrhodium compounds or rhodium acetylacetonate. Rhodium-halogen compounds are less satisfactory because of the corrosive nature of the halide ions. Preference is given to using rhodium oxide and, in particular, rhodium nitrate, rhodium acetate and rhodium 2-ethylhexanoate.

Figure 1:
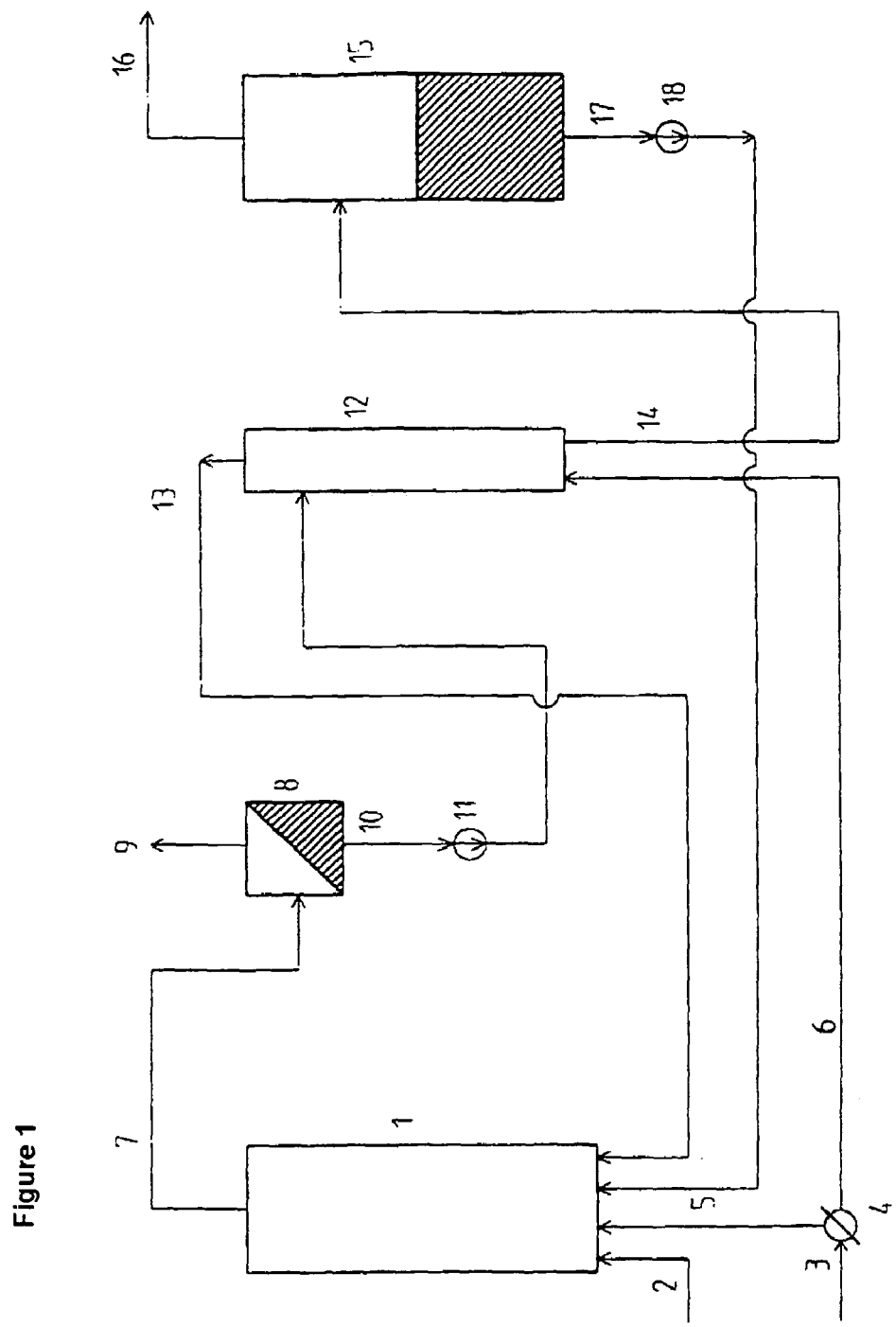
FIGS. 1 and 2 are two variations of the hydroformylation process of the invention.

In the process variant outlined in FIG. 1, olefin is fed in, via line 2, at the bottom of the hydroformylation reactor 1 which is completely filled with liquid. The fresh synthesis gas stream fed in via line 3 is divided in the splitter 4 into the substream conveyed via line 5 to the bottom of the hydroformylation reactor 1 and the substream conveyed via line 6 to the bottom of the extraction column 12. At the top of the hydroformylation reactor 1, the liquid, catalyst-containing product stream is taken off via line 7 and passed to a gas/liquid separator 8. The offgas obtained here is discharged via line 9; it comprises predominantly carbon monoxide, hydrogen and small amounts of unreacted olefinically unsaturated compound and reaction product. The liquid product stream is conveyed via line 10 with the aid of a pump 11 to the extraction column 12. Via line 6, synthesis gas is introduced at the bottom of the extraction column 12 and flows toward the liquid product stream, resulting in further reaction of the residual amount of olefinically unsaturated compound dissolved in the liquid product stream to form aldehydes. In the extraction column 12, heat is likewise transferred from the hot, liquid product stream to the synthesis gas which leaves the top of the extraction column 12 and is recirculated via line 13 together with residual traces of olefinically unsaturated compound back to the hydroformylation reactor 1. The product stream which had been freed of olefinically unsaturated compound and comprises crude aldehyde solvent and catalyst is passed via line 14 to the vaporizer 15 in which the crude aldehyde is vaporized and is taken off via line 16 and passed to further work-up, which is carried out in a manner known per se. The high-boiling solution which is obtained in the vaporizer and comprises the high-boiling aldehyde condensation products with or without other, added high-boiling solvents and the dissolved rhodium catalyst is recirculated via line 17 with the aid of the pump 18 back to the hydroformylation reactor 1.

Figure 2:
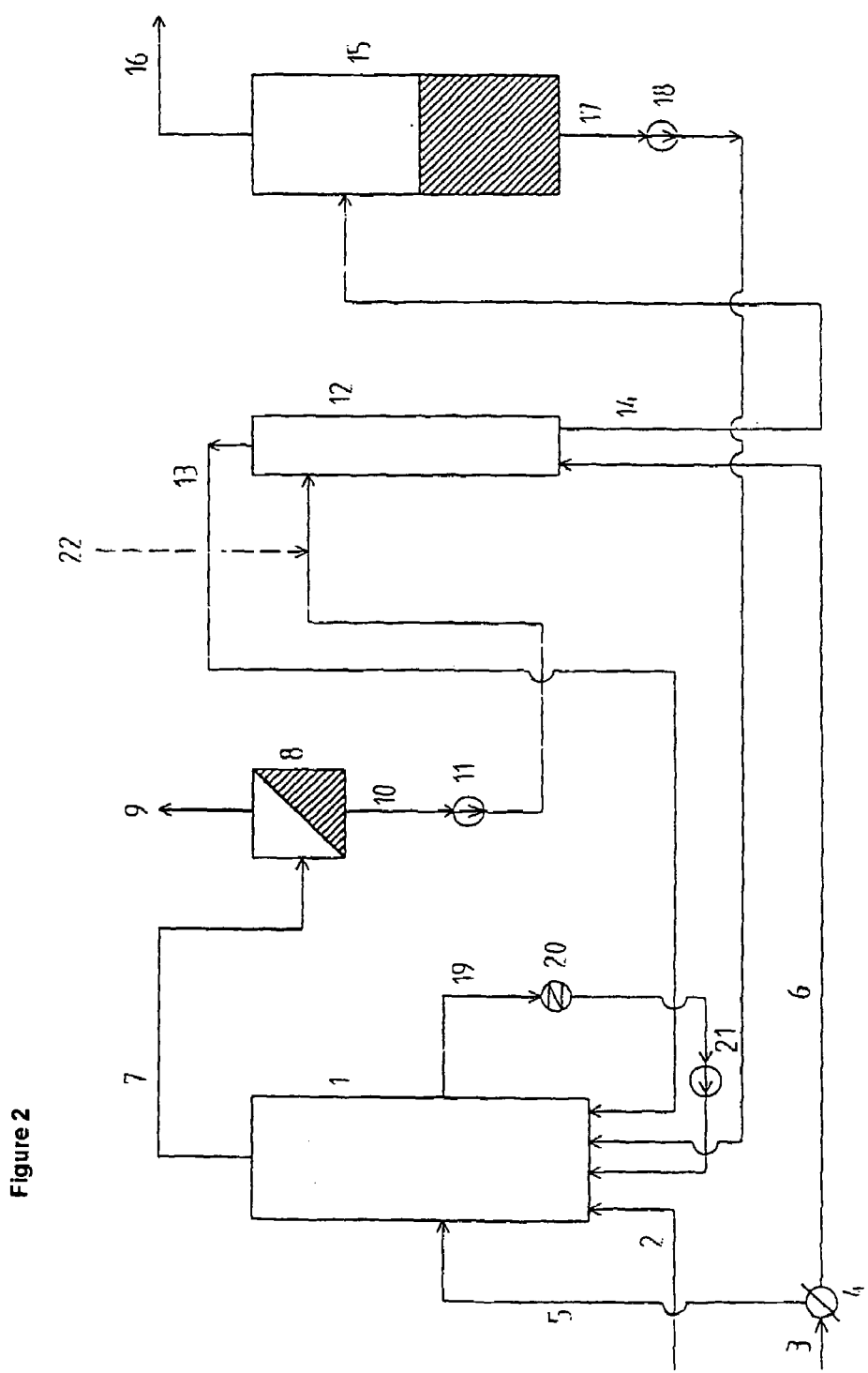

The process variant shown in FIG. 2 differs from that shown in FIG. 1 in that the hydroformylation reactor 1 is operated as a loop reactor. For this purpose, a liquid substream is discharged via line 19, cooled in the heat exchanger 20 and conveyed by means of the pump 21 back into the reactor in order to maintain a circulation of liquid. In the process variant shown in FIG. 2, fresh synthesis gas is supplied via line 3 and one of the substreams of synthesis gas obtained in the splitter 4 is conveyed via line 5 to the middle part of the hydroformylation reactor 1. In a further embodiment of the process of the invention, additional synthesis gas can, if desired, be fed via line 22, which is shown as a broken line in FIG. 2, into line 10 upstream of the point at which it enters the extraction column 12. The plant components denoted by the reference numerals 2, 6 to 9, 11, 13 to 18 correspond to those in FIG. 1.

The invention is illustrated by the following examples but is not restricted to the embodiments described.

EXAMPLE 1

The hydroformylation of propylene was carried out in the plant variant shown in FIG. 2 under the following reaction conditions.

| | |
|---|---|
| Reactor volume: | 14 liters |
| Pressure: | 2.1 MPa |
| Temperature: | 120° C. |
| Synthesis gas feed (total): | 4 standard m³/h* |
| Propylene feed: | 5.0 kg/h |
| Residence time of the liquid reactor contents: | 0.7 h |
| Rhodium concentration: | 600 ppm |
| Triphenylphosphine concentration, based on the total reaction solution | 30% |

(*)The unit standard m³/h means standard cubic meters per hour, i.e. 1 cubic meter at a temperature of 273 K and a pressure of 1013 mbar per hour.

Propylene was introduced from below via line 2 into the hydroformylation reactor 1 which was filled with catalyst solution. Fresh synthesis gas was brought via line 3 to the splitter 4 which was set so that all the synthesis gas brought via line 3 was fed to line 6. The total amount of synthesis gas fed in flowed firstly through the extraction column 12 and subsequently via the line 13 to the bottom of the hydroformylation reactor 1. By means of the liquid circuit 19, the hydroformylation reactor 1 was operated according to the principle of a loop reactor, with the heat of reaction being removed via the heat exchanger 20. The propylene conversion in the hydroformylation reactor was 85%. The liquid output from the reactor was conveyed via line 7 into the gas/liquid separator 8 from which offgas was discharged via line 9. The temperature of the liquid stream obtained, which contained about 5% by weight of propylene, based on the homogeneous, liquid solution, was about 115° C. This solution flowed via line 10 with the aid of the pump 11 to the 1st tray, of the extraction column counted from the top of the column. Synthesis gas was fed in via line 6 and conveyed in countercurrent to the liquid stream. The reaction temperature could be maintained in a zone amounting to 20% of the length of the extraction column and extending from the top of the column. The product from the top of the extraction column, comprising predominantly synthesis gas and propylene, was recirculated via line 13 to the bottom of the hydroformylation reactor 1. The liquid output from the extraction column 12 had a temperature of 85° C. and still contained 0.3% by weight of residual propylene, based on the total amount of liquid. This liquid stream was passed via line 14 to the vaporizer 15, which was operated at a temperature of 145° C. and atmospheric pressure. Crude aldehyde was obtained at the top of the vaporizer 15 and discharged via line 16, while catalyst solution was recirculated via line 17 with the aid of the pump 18 to the hydroformylation reactor 1. The crude aldehyde discharged via line 16 was firstly condensed in a known manner, with the offgas comprising residual amounts of propylene, inerts, for example propane, and other volatile constituents being discharged and the liquid crude aldehyde being worked up further (not shown in FIG. 2).

EXAMPLE 2

The procedure of Example 1 was repeated, with the sole exception that additional synthesis gas was fed via line 22 into line 10. The amount of synthesis gas introduced via line 22 was between 10–20%, based on the synthesis gas fed into the hydroformylation reactor. The addition of synthesis gas resulted in further reaction of propylene in line 10 and led to a temperature increase to 142° C. and to a decrease in the residual propylene content to 4% by weight, based on the total solution. Compared to the embodiment of Example 1, the homogeneous, liquid stream introduced via line 10 into the extraction column 12 therefore had a higher temperature and a lower residual propylene content. Likewise, compared to Example 1, the temperature of the liquid stream leaving the extraction column 12 via line 14 had increased to 115° C. Propylene could no longer be detected in the stream.

EXAMPLE 3

Example 3 was carried out using the procedure of Example 2, with the sole exception that the synthesis gas introduced was divided into two equal substreams in the splitter 4 and one synthesis gas substream was conveyed via line 5 and introduced into the middle part of the hydroformylation reactor 1. Compared to Example 1, the propylene conversion could be increased by 6.5% to 90.5%, while the other results corresponded to the results from Example 2.

The invention claimed is:

1. A process for reacting olefinically unsaturated compounds with synthesis gas in the presence of a catalyst solution comprising rhodium and organic phosphorus(III) compounds in a hydroformylation reactor, in which the homogeneous, liquid reactor output comprising crude aldehyde and catalyst is passed to a gas/liquid separator and the homogeneous, liquid stream obtained is treated in an extraction column operated in countercurrent with synthesis gas and the liquid output from the extraction column is fed into a vaporizer in which crude aldehyde and catalyst solution are separated from one another, wherein synthesis gas is added to the homogeneous, liquid stream obtained from the gas/liquid separator before this stream enters the extraction column, and the homogeneous, liquid stream is introduced at a temperature of from 110 to 150° C., into the upper part of the extraction column.

2. The process of claim 1, wherein synthesis gas is fed into the hydroformylation reactor at one or more feed points.

3. The process of claim 1 wherein the synthesis gas fed to the hydroformylation reactor is composed of fresh synthesis gas and the synthesis gas is recirculated via the extraction column.

4. The process of claim 1 wherein fresh synthesis gas is introduced into the middle part of the hydroformylation reactor and the synthesis gas which is recirculated via the extraction column is fed in via the lower part of the hydroformylation reactor.

5. The process of claim 1 wherein the homogeneous liquid stream obtained from the gas/liquid separator is introduced on the first tray of the extraction column, counted from the top of the column.

6. The process of claim 1 wherein the extraction column is a tray column, a column containing ordered packing or a column containing random packing elements.

7. The process of claim 1 wherein the extraction column has 10 to 40, theoretical plates.

8. The process of claim 1 wherein the concentration of organic phosphorous(III) compounds in the homogeneous reaction solution is from 15 to 60% by weight, based on the homogeneous reaction solution.

9. The process of claim 8, wherein the concentration of organic phosphorus(III) compounds in the homogeneous reaction solution is from 25 to 50% by weight, based on the homogeneous reaction solution.

10. The process of claim 1 wherein the rhodium concentration of the homogeneous reaction solution is from 1 to 1000 ppm, based on the homogeneous reaction solution.

11. The process of claim 10, wherein the rhodium concentration of the homogenous reaction is from 10 to 800 ppm, based on the homogeneous reaction solution.

12. The process of claim 7 wherein the extraction column has 15 to 25 theoretical plates.

* * * * *